(12) United States Patent
Kolesnychenko et al.

(10) Patent No.: US 8,441,629 B2
(45) Date of Patent: May 14, 2013

(54) OPTICAL DETECTION SYSTEM FOR MONITORING RTPCR REACTION

(75) Inventors: Aleksey Kolesnychenko, AE Eindhoven (NL); Jorrit E. De Vries, AE Eindhoven (NL); Jozef C. M. Versleegers, AE Eindhoven (NL); Michiel De Jong, AE Eindhoven (NL); Theodoor B. J. Haddeman, AE Eindhoven (NL); Louis Stroucken, AE Eindhoven (NL)

(73) Assignee: Biocartis SA, Lausanne (CH)

( * ) Notice: Subject to any disclaimer, the term of this patent is extended or adjusted under 35 U.S.C. 154(b) by 0 days.

(21) Appl. No.: 13/273,801

(22) Filed: Oct. 14, 2011

(65) Prior Publication Data

US 2012/0033210 A1 Feb. 9, 2012

Related U.S. Application Data

(63) Continuation of application No. PCT/CH2010/000094, filed on Apr. 9, 2010.

(30) Foreign Application Priority Data

Apr. 15, 2009 (EP) ...................................... 09157910

(51) Int. Cl.
 *G01N 1/10* (2006.01)
(52) U.S. Cl.
 USPC .......... 356/246; 356/440; 356/301; 435/91.2; 435/287.2; 422/82.05
(58) Field of Classification Search .......... 356/244–246, 356/432–440, 300–301, 326; 435/6, 287.2, 435/91.2; 422/82.05, 68.1
See application file for complete search history.

(56) References Cited

U.S. PATENT DOCUMENTS

| | | | |
|---|---|---|---|
| 3,607,134 A | 9/1971 | McIntyre | |
| 3,633,877 A | 1/1972 | Bodine | |
| 4,057,148 A * | 11/1977 | Meyer et al. | ..................... 211/74 |
| 4,234,540 A | 11/1980 | Ginsberg et al. | |
| 4,256,697 A | 3/1981 | Baldwin | |
| 4,371,498 A | 2/1983 | Scordato et al. | |
| 4,571,087 A | 2/1986 | Ranney | |
| 4,849,340 A | 7/1989 | Oberhardt | |
| 4,857,274 A | 8/1989 | Simon | |
| 4,857,453 A | 8/1989 | Ullman et al. | |
| 4,874,137 A | 10/1989 | Chiba | |
| 4,943,522 A | 7/1990 | Eisinger et al. | |

(Continued)

FOREIGN PATENT DOCUMENTS

| | | |
|---|---|---|
| CH | 667599 A5 | 10/1988 |
| DE | 19820466 A1 | 11/1999 |

(Continued)

OTHER PUBLICATIONS

International Search Report dated Aug. 19, 2010 from PCT/CH2010/000094.

*Primary Examiner* — Hoa Pham
(74) *Attorney, Agent, or Firm* — Kusner & Jaffe

(57) ABSTRACT

An optical detection system for monitoring real-time PCR reactions in a plurality of sample chambers with a plurality of optical units is provided. Due to a relative movement, the optical units are relative to the sample chambers, color multiplexing and space multiplexing are combined for optically detecting pathogens in a sample during the process of the PCR and delivering a quantitative result.

19 Claims, 4 Drawing Sheets

U.S. PATENT DOCUMENTS

| | | | |
|---|---|---|---|
| 4,965,047 | A | 10/1990 | Hammond |
| 4,983,523 | A | 1/1991 | Li et al. |
| 5,004,583 | A | 4/1991 | Guruswamy et al. |
| 5,096,669 | A | 3/1992 | Lauks et al. |
| 5,133,937 | A | 7/1992 | Frackleton et al. |
| 5,147,609 | A | 9/1992 | Grenner |
| 5,219,526 | A | 6/1993 | Long |
| 5,229,580 | A | 7/1993 | Chioniere |
| 5,296,374 | A | 3/1994 | Culshaw et al. |
| 5,397,537 | A | 3/1995 | Kanda et al. |
| 5,500,187 | A | 3/1996 | Deoms et al. |
| 5,504,007 | A | 4/1996 | Haynes |
| 5,504,013 | A | 4/1996 | Senior |
| 5,512,159 | A | 4/1996 | Yoshioka et al. |
| 5,578,495 | A | 11/1996 | Wilks |
| 5,589,136 | A | 12/1996 | Northrup et al. |
| 5,597,532 | A | 1/1997 | Connolly |
| 5,609,822 | A | 3/1997 | Carey et al. |
| 5,609,823 | A | 3/1997 | Harttig et al. |
| 5,622,871 | A | 4/1997 | May et al. |
| 5,627,041 | A | 5/1997 | Shartle |
| 5,726,026 | A | 3/1998 | Wilding et al. |
| 5,746,978 | A | 5/1998 | Bienhaus et al. |
| 5,770,029 | A | 6/1998 | Nelson et al. |
| 5,788,928 | A | 8/1998 | Carey et al. |
| 5,843,680 | A | 12/1998 | Manian et al. |
| 5,856,174 | A | 1/1999 | Lipshutz et al. |
| 5,882,903 | A | 3/1999 | Andrevski et al. |
| 5,912,134 | A | 6/1999 | Shartle |
| 5,928,880 | A | 7/1999 | Wilding et al. |
| 5,928,907 | A | 7/1999 | Woudenberg et al. |
| 5,945,334 | A | 8/1999 | Besemer et al. |
| 5,994,056 | A | 11/1999 | Higuchi |
| 6,077,669 | A | 6/2000 | Little et al. |
| 6,100,084 | A | 8/2000 | Miles et al. |
| 6,143,573 | A | 11/2000 | Rao et al. |
| 6,210,881 | B1 | 4/2001 | Little et al. |
| 6,329,139 | B1 | 12/2001 | Nova et al. |
| 6,369,893 | B1 | 4/2002 | Christel et al. |
| 6,391,541 | B1 | 5/2002 | Petersen et al. |
| 6,426,225 | B1 | 7/2002 | Lewis et al. |
| 6,431,476 | B1 | 8/2002 | Taylor et al. |
| 6,440,725 | B1 | 8/2002 | Pourahmadi et al. |
| 6,521,181 | B1 | 2/2003 | Northrup et al. |
| 6,524,532 | B1 | 2/2003 | Northrup |
| 6,551,817 | B2 | 4/2003 | Besemer et al. |
| 6,565,815 | B1 | 5/2003 | Chang et al. |
| 6,664,104 | B2 | 12/2003 | Pourahmadi et al. |
| 6,699,711 | B1 | 3/2004 | Hahn et al. |
| 6,713,297 | B2 | 3/2004 | McMillan et al. |
| 6,783,736 | B1 | 8/2004 | Taylor et al. |
| 6,818,185 | B1 | 11/2004 | Petersen et al. |
| 6,878,540 | B2 | 4/2005 | Pourahmadi et al. |
| 6,881,541 | B2 | 4/2005 | Petersen et al. |
| 6,887,693 | B2 | 5/2005 | McMillan et al. |
| 6,893,879 | B2 | 5/2005 | Petersen et al. |
| 6,987,018 | B2 | 1/2006 | Taylor et al. |
| 7,188,001 | B2 | 3/2007 | Young et al. |
| 7,507,575 | B2 | 3/2009 | Bedingham et al. |
| 7,569,346 | B2 | 8/2009 | Petersen et al. |
| 7,709,249 | B2 * | 5/2010 | Bedingham et al. ........ 435/288.7 |
| 8,236,504 | B2 * | 8/2012 | Kordunsky et al. .......... 435/6.12 |
| 2001/0046051 | A1 * | 11/2001 | Banerjee ...................... 356/436 |
| 2002/0019060 | A1 | 2/2002 | Petersen et al. |
| 2002/0084329 | A1 | 7/2002 | Kaye et al. |
| 2004/0200909 | A1 | 10/2004 | McMillan et al. |
| 2005/0042137 | A1 | 2/2005 | Petersen et al. |
| 2006/0019379 | A1 | 1/2006 | Taylor et al. |
| 2006/0027686 | A1 | 2/2006 | Taylor et al. |
| 2006/0030038 | A1 | 2/2006 | Taylor et al. |
| 2008/0057572 | A1 | 3/2008 | Petersen et al. |
| 2010/0068706 | A1 | 3/2010 | Pourahmadi et al. |
| 2010/0086991 | A1 * | 4/2010 | Fish .......................... 435/286.1 |
| 2010/0105035 | A1 * | 4/2010 | Hashsham et al. ............... 435/6 |
| 2011/0151550 | A1 * | 6/2011 | Sagner et al. ............... 435/287.2 |

FOREIGN PATENT DOCUMENTS

| | | |
|---|---|---|
| EP | 0271448 A2 | 6/1988 |
| EP | 0337690 A1 | 10/1989 |
| EP | 0512334 A2 | 11/1992 |
| EP | 0757830 B1 | 12/1998 |
| EP | 0706649 B1 | 1/2001 |
| EP | 1383602 B1 | 6/2006 |
| EP | 1181098 B1 | 7/2006 |
| EP | 0915173 B1 | 1/2007 |
| EP | 1 024 355 B1 | 3/2008 |
| EP | 1179585 B1 | 7/2008 |
| GB | 938163 A2 | 10/1963 |
| WO | 9511454 A1 | 4/1995 |
| WO | 9529473 A1 | 11/1995 |
| WO | 9838487 A2 | 9/1998 |
| WO | 9958637 A2 | 11/1999 |
| WO | 2006136990 A2 | 12/2006 |
| WO | 2010064160 A1 | 6/2010 |

* cited by examiner

OPTICAL DETECTION SYSTEM FOR MONITORING RTPCR REACTION

CROSS REFERENCE TO RELATED APPLICATIONS

This application is a continuation of International Application Serial No. PCT/CH2010/000094 filed Apr. 9, 2010, now pending, which claims the benefit under 35 U.S.C. §119 (a) of European Patent Application No. EP09157910.2, filed Apr. 15, 2009, the entire contents of both of which are incorporated herein by reference.

BACKGROUND OF THE INVENTION

1. Field of the Invention

The disclosure relates to optical detection systems. In particular the disclosure relates to an optical multiplexing system for detecting sample components in at least two different sample chambers, a method for detecting sample components in at least two different sample chambers, a computer program element and a computer-readable medium.

2. Description of Related Art

The polymerase chain reaction (PCR) is a technique widely used in molecular biology. It derives its name from one of its key components, a deoxyribonucleic acid (DNA) polymerase used to amplify a piece of DNA by in vitro enzymatic replication. As PCR progresses, the DNA generated is used as a template for replication. This sets in motion a chain reaction in which the DNA template is exponentially amplified. With PCR it is possible to amplify a single or few copies of a piece of DNA across several orders of magnitude, generating millions or more copies of the DNA piece. PCR can be extensively modified to perform a wide array of genetic manipulations.

Thereby thermal cyclers as laboratory apparatuses are used to amplify segments of DNA via the PCR process. The cycler rises and lowers the temperature surrounding of the samples within the cartridges or sample chambers in discrete, pre-programmed steps.

In molecular biology, real-time PCR (rtPCR) or also called quantitive real-time PCR is used as a laboratory technique based on the PCR reaction to amplify and simultaneously quantify a targeted DNA molecule. It enables both detection and quantification of a specific sequence in a DNA sample.

SUMMARY OF THE INVENTION

It may be an object of the disclosure to provide for an improved detection of components of a sample.

Sample chambers: In context of the present disclosure any cartridge, vessel or container being able to contain a sample especially a liquid sample shall be comprised in the term "sample chamber". Especially cartridges providing for PCR chambers or PCR containers for example with a desired optical transparency or being for example formed out of a material such as polypropylene or any other thermoplastic polymer are comprised in the term "sample chamber" in the context of the disclosure.

Light source: In the context of the present disclosure any kind of device being able to emit a monochromatic or broadband electromagnetic field shall be understood under the term "light source". Furthermore also arrays of a plurality of light sources with equal or different characteristics concerning frequency, polarization, flux, electrical input power or technology used to emit photons shall be comprised under the term "light source". For example, light emitting diodes (LED), organic light emitting diode (OLED), polymer light emitting diode (PLED), quantum dot based light sources, white light sources, halogen lamps, lasers, solid-state lasers, laser diodes, micro wire lasers, diode solid-state lasers, vertical cavity surface emitting lasers, phosphor-coated LEDs, thin-film electroluminescent devices, phosphorescence OLEDs, inorganic/organic LEDs, LEDs using quantum dot technologies, LED arrays, flood light systems using LEDs, white LEDs, filament lamps, arc lamps, gas lamps and fluorescent tubes shall be comprised within the term "light source".

Detector: Any device being able to detect electromagnetic radiation is comprised within the term "detector". For example a charge coupled device (CCD), a photodiode, a photodiode array. Furthermore the detector may be adapted in such a way that detected radiation and the corresponding generated information may be delivered to a storage, a computer or another control unit.

Sample: The term "sample" as used hereinafter shall refer to any kind of substance comprising one or several components that can be detected by optical detection, for example by optical excitation and subsequent optical read out. For example, biochemical substances may be analyzed in the context of the present disclosure. Furthermore the sample may be a substance used in the field of molecular diagnostics, clinical diagnostics, gene and protein expression arrays. Components of the sample, which components are to be detected may especially be any substance that can be copied by PCR.

Frequency/Wavelength: As long as not stated differently in the description the terms "frequency" and "wavelength" are electromagnetic frequencies and electromagnetic wavelength.

According to an exemplary embodiment of the disclosure, an optical multiplexing system for detecting sample components in at least two different sample chambers is presented. The system comprises a first optical unit and a second optical unit, wherein the first optical unit and the second optical unit are spatially separated from each other. Furthermore the first optical unit comprises a first light source and a first detector and the second optical unit comprises a second light source and a second detector. In addition to that the system is adapted for receiving the at least two chambers at positions corresponding to the optical units so that the first and second light source respectively illuminate at least one sample chamber and the first and second detector respectively receive light from at least one sample chamber. This includes the first light source illuminating the chamber located at the position corresponding to the first optical unit and the second light source illuminating the chamber located at the position corresponding to the second optical unit. This also includes the first detector receiving light from the chamber located at the position corresponding to the first optical unit, and the second detector receiving light from the chamber located at the position corresponding to the second optical unit. Furthermore the system is adapted for a relative movement of the first and second optical unit relative to the two chambers. In other words, the first and the second optical units are mounted at the system in such a way that a movement of the first and second optical unit relative to the two chambers in a received position can be caused by the control unit. Thus the system is arranged in such a way, that the relative movement can be performed after the at least two chambers have been inserted into the system.

This optical multiplexing system makes it possible to simultaneously detect components like e.g. pathogens in at least two different and spatially separated sample chambers.

In other words, it is possible to simultaneously irradiate at least two different sample chambers with the light of two different light sources simultaneously and simultaneously detect the re-emitted light of the respective optically excited samples in the two different sample chambers with a respective detector.

Thereby transmission measurements of the samples are possible in which the sample (the chamber) is arranged in passage way between the light source and the respective detector. But also measurements, in which the light originating from the sample (or from the components of the sample) is deflected by mirrors or other optical components are possible.

As the optical units may e.g. detect fluorescence light which may have no preference direction after excitation, the detectors may be positioned if desired at any position around the sample chambers, when the chambers are in a received position.

Thereby each optical unit may be optimized for an optical excitation of a sample and an optical read out of the sample with respect to specific but different frequencies i.e. colors. In detail the first light source may irradiate a first frequency that may be optimized or matched for exciting a first dye or fluorochrome in a sample and the first detector may be optimized to detect a second frequency emitted from the excited dye or the excited fluorochrome of the first sample. However, the second light source may be optimized to excite a second dye or fluorochrome in a second sample by irradiating the second sample with a third frequency. Furthermore the second detector might be optimized to detect an emitted fourth frequency by the second dye or fluorochrome in the second sample.

In other words, the optical multiplexing system according to this exemplary embodiment enables a user to do so-called "color multiplexing" by using multiple samples labeled with different dyes or fluorochromes simultaneously in one measurement apparatus. This enables a simultaneous detection via the detectors of several pathogens present in a single sample. Thereby this single patient sample may be divided into for example two samples which can be filled into the two different sample chambers.

Furthermore the disclosure provides for so-called "space multiplexing" in which multiple PCR volumes in the different sample chambers may contain a different set of primers. This further enables a simultaneous detection via the detectors of several pathogens present in a single sample.

In other words, the optical multiplexing system is an optical detection system comprising several optical units each able to detect different PCR reactions by monitoring PCR probes in the sample chambers having for example different fluorescent spectra. Thereby the first and the second optical units are arranged in such a way that each optical unit has an optical access to one of the sample chambers. In this way all optical units can simultaneously monitor PCR reactions in multiple different chambers therefore space multiplexing is achieved. The color multiplexing is achieved by causing a relative movement of the first and the second optical unit relative to the two chambers, with respect to the fact that the first and the second optical unit may be equipped with different light sources and different detectors in order to be able to optically excite and optically readout different dyes or for example different fluorochromes in the at least two different samples.

Nevertheless if desired it is possible to equip the first and the second optical unit with identical light sources and/or identical detectors. The optical multiplexing system may also comprise a control unit, which control unit is adapted to cause the relative movement of the first and second optical unit relative to the at least two sample chambers.

It shall explicitly be noted that also a plurality greater than two different sample chambers may be comprised in the optical multiplexing system. For example 3 or more different sample chambers are possible. In addition to that a plurality of optical units greater than 2 is a possible configuration. For example 3 or more optical units may be comprised by the system. Thereby it might be advantageous that the amount of optical units corresponds with the amount of chambers. Nevertheless it is possible that more optical units than chambers are possible as well as a configuration in which more chambers than optical units are present is possible.

Furthermore, it shall explicitly be noted that in this and any other exemplary embodiment of the disclosure if not stated differently a relative movement might be caused by a movement of the first and the second optical unit relative to the stationary two chambers, by a movement of the two chambers relative to the stationary optical units or by a first movement of the optical units and in addition by a second movement of the two chambers.

By inserting the at least two chambers into the system the system receives the at least two chambers at positions that correspond to the optical units, which means an optical measurement can be performed by the respective optical unit at the respective sample chamber. For example, a sample holder where PCR cartridges might be fixed at is inserted into the system in such a way that the two or more different sample chambers are positioned in front of the optical unit that each optical unit has an optical access to a single sample chamber. Therefore, the sample chamber that can be formed as a PCR chamber may provide an optical access with an optical transmission that has a desired value. Furthermore materials may be used for the PCR chamber that may exhibit no or at least a desired low value of auto-fluorescence at the excitation wavelengths used with the first and second light sources. This optical access of the PCR chamber may for example be realized by providing at least one part of the PCR chamber made from optically transparent materials such as polypropylene in e.g. a foil form.

Furthermore each optical unit may comprise an optical bandpass, a filter, a lens, a dichroic mirror or other optical components in order to guide photons emitted from the light source or photons emitted from the excited sample in a desired way.

The optical multiplexing system makes it possible to simultaneously do at least two measurements that use at least two different optical wavelengths and that are performed at two spatially separated sample chambers. The system may rotate after this first and second measurement at which the system is in a first position into a second position. In the second position each sample chamber is optically excited and read out by the other wavelength compared to the first position.

In case of a simultaneous rotation of all optical units around the stationary sample chambers the device guides the electrical and/or electronical leads from the surrounding of the system (e.g. from the control unit) to the light sources and to the detectors in such a way, that the guiding of these leads is not affected by the rotation. Thus this exemplary embodiment overcomes the problem of the integration of active optical components into a rotating system which components have to be controlled from outside of the system.

Furthermore in such a case a high precision movement of the rotating optical head comprising all optical units is necessary, because after each rotation each propagation path of the photons emitted by each respective optical unit has to be matched with the optical access of the respective sample chamber or PCR chamber.

As this system shall be configured to do a huge amount of measurement cycles durability requirements of the rotating optical head have to be fulfilled. This exemplary embodiment meets all these requirements.

Thus a fast and efficient detection possibility for detecting several pathogens in one or more samples is presented by the disclosure.

In case rtPCR shall be performed by the system heaters for each sample chamber may be comprised by the system to carry out a PCR protocol. The control unit e.g. may control different PCR reactions within the different sample chambers and may also control a simultaneous optical excitation and read out of the chambers in order to quantify the amount of one or more pathogens within the samples. This quantification may be based on the detected e.g. fluorescence signals, which may further be processed by a PC or the control unit.

It shall explicitly be noted that according to an exemplary embodiment of the disclosure moving one optical unit from a first position to a second position means that the optical unit moves from a first process chamber to a second process chamber and that, similarly, a second optical unit simultaneously moves from a third process chamber to a fourth process chamber. An important aspect of the disclosure is that different optical units may simultaneously make different analyses of different sample chambers, but that each optical unit sequentially may address each process chamber due to the changes in position caused by the relative movement.

As described above the disclosure offers the possibility of rotating the set of process chambers instead of the optical units. The important thing is the motion of the optical assembly relative to the process chambers.

In other words, after a single detection cycle, an optical unit is moved to the next position, e.g. by rotation, so that at least some of the optical units move from the previous chamber to the next chamber. At the new position again a single color is detected. As a result, the chamber that was first serviced by the first optical unit is now serviced by a second optical unit detecting a color different from the color detected by the first optical unit.

In principle a plurality of different colors may be emitted by one sample inside a cartridge. For example four or six different colors may be emitted from each sample chamber. Nevertheless each optical unit may be arranged in such a way, that it detects a single color. A different number of colors is also possible.

According to an exemplary embodiment of the disclosure the optical multiplexing system is arranged in such a way, that during the execution of the relative movement electronical leads for the light sources and/or the detectors are rolled up around a rotational axis of the relative movement.

According to another exemplary embodiment of the disclosure the optical multiplexing system further comprises a motor, wherein the motor is adapted to cause the relative movement.

Thereby the motor may be a device comprising mechanical, electrical, electromechanical, and/or magnetical technology being able to cause the relative movement. Furthermore the control unit is adapted to cause the motor to initiate or cause the relative movement.

According to another exemplary embodiment of the disclosure the relative movement is a rotating movement.

The cartridge, which may also be part of the system, may comprise a circular holder containing the sample chambers and other units. The sample chambers being for example PCR chambers may thus be fixed in a circular way in order to insert the holder into the part of the system comprising the optical units. This part will further be described with the term optical head. A plurality of optical units may be also arranged in a circular manner at the optical head. In this exemplary embodiment the distances between the positions of the different sample chambers at the holder of the sample chambers may be equal to the distances between the optical units fixed at the optical head. Therefore, if the relative movement is caused each of the sample chambers can be positioned by a partial rotation of the optical head in front of an optical unit. Thereby a partial rotation shall be understood as a rotation that causes a difference in position before and after the rotation of x°, wherein x is smaller than 360. In other words, by sequentially rotating the optical head with all optical units each sample chamber can be excited and read out by each optical unit sequentially. By using different dyes or different primers in the different samples and by using different wavelengths and different detectors a combination of space multiplexing and color multiplexing can be achieved. Therefore, in a fast and an inexpensive way several pathogens may be detected by the optical multiplexing system within one sample that may be divided in different samples that are filled into the different sample chambers.

According to another exemplary embodiment of the disclosure the system comprises a rotation frame wherein the first and second optical units are fixed at the rotation frame and wherein the motor causes the relative movement by rotating the rotation frame.

In other words, the relative movement is performed in such a way, that the at least two optical units move synchronously.

The rotation frame may for example comprise an upper rotation plate and a lower rotation plate wherein the lower rotation plate may for example be shaped in circular manner. The upper rotational plate may for example be shaped polygonally. Furthermore the upper and lower rotation plates are arranged in such a way, that the optical units can be fixed between them. Furthermore the upper and lower rotation plates are arranged in such a way, that electrical leads for the sources and the detectors may be guided through the upper rotation plate.

Furthermore a flexible band of leads may be rolled up around a rotational axis which band is elongated during rotation perpendicular to the rotational axis. With this band comprising electrical leads control means can be connected to the rotation frame in order to control the different light sources and the different detectors. Due to the rotation caused by the motor each sample chamber can optically be excited and read out by each optical unit. In case of e.g. four sample chambers four rotations are necessary to position each sample chamber once in front of the first, second, third, fourth and fifth optical units. In case of for example twelve optical units twelve rotations would be necessary to reach each sample chamber by each optical unit.

A circular arrangement of firstly the sample chambers and secondly the optical units may have the advantage of reducing the space needed for the whole configuration of the system.

Furthermore the system is arranged in such a way, that the optical units can be selectively continuously be placed by the movement at any position along a circumference. In other words each angle between two positions of one optical unit before and after the movement is possible. If desired, the system is arranged in such a way, that the optical units can only be placed by the movement at concrete stop positions along a circumference.

According to another exemplary embodiment of the disclosure the relative movement is a linear movement.

If desired, the relative movement can be realized as a linear movement in order to linearly scan the different sample chambers with the optical units.

According to another exemplary embodiment of the disclosure the system further comprises at least one heater, wherein the heater is adapted to cause a thermal cycling in at least one sample chamber.

It shall explicitly be noted that the plurality of heaters may also include a plurality of heaters per sample chamber can be supplied by the system. Therefore, the optical multiplexing system is enabled to perform complete PCR protocols and therefore causing complete PCR reactions within the different sample chambers. Therefore, it is possible that a PCR protocol provided to the control unit which control unit controls a heat generation at the respective sample chambers via the heaters. Thus real-time PCR measurements can be provided by the system, as the optical excitation and readout can respectively be done by each optical unit, if desired simultaneously.

In other words the optical multiplexing system is working as a thermocycler that includes a complete optical readout system in one device to cause polymerase chain reaction and simultaneously quantify a targeted and amplified DNA molecule by rotating an optical head relative to the sample chambers.

According to another exemplary embodiment of the disclosure the heater is optically transparent with respect to at least one of the first and the second light source.

Therefore, the heater meets both thermal and optical requirements. For example, it is possible that the optical transparency of the heater is greater than 80% in a spectral range between 300 nm and 800 nm wavelength. Furthermore the heater material may have a negligible autofluoresence at excitation wavelengths between 300 nm and 800 nm. But also other optical characteristics of the heaters are possible. In other words, the heaters are selected and matched optically with the used wavelengths of the different light sources.

According to another exemplary embodiment of the disclosure a molecular diagnostic device for analyzing a sample is presented. The device comprises an optical multiplexing system according to one of the embodiments mentioned before or hereinafter.

The molecular diagnostic device may be adapted to receive a sample e.g. a liquid sample for example via sample leads. Furthermore the molecular diagnostic device may process the sample with different various functionalities like heating, cooling, mixing or other treating functionalities. By using and may be by controlling the optical multiplexing system, the device is adapted to carry out a whole measurement process of a sample comprising for example polymerase chain reaction. Thus a fully automated device for detecting sample components is presented that realizes the advantageous combination of spatial multiplexing and of color multiplexing as described above and in the following.

According to another exemplary embodiment of the disclosure the system is adapted to cause different PCR reactions in the two chambers with the heater and wherein the optical units are adapted to detect different products of different PCR reactions.

In other words, the optical multiplexing system enabling color multiplexing and space multiplexing provides for a complete sample-in-answer-out system regarding rtPCR. In other words the system may carry out a PCR protocol and create different temperature progressions at the different sample chambers due to different heaters, thus causing an amplification of desired DNA. Simultaneously, the device is able with the optical units to screen optically such samples for the presence of various pathogens. Therefore the specific chemical reactions during the PCR are optically detected firstly with different optical units using different optical characteristics like described above. This rtPCR device may simultaneously excite and detect several pathogens at spatially divided different sample chambers and the functionality to rotate the optical units to the next sample chamber and subsequently scan sample chamber with another optical wavelength leads to a fast and efficient rtPCR system due to color and space multiplexing.

In other words, this sample-in-answer-out optical detection system for monitoring rtPCR reactions heats and cools via the at least one heater the sample chambers to achieve the temperature required at each step of the reaction. Thereby the Peltier effect may be used which permits both heating and cooling of the sample chamber by reversing the electric current. Thereby the PCR may consist of a series of for example twenty to forty repeated temperature changes so-called cycles. Thereby each cycle may consist of two to three discrete temperature steps.

According to another exemplary embodiment of the disclosure a method for detecting sample components in at least two different chambers is presented. Thereby, the method comprises the steps providing for a first optical unit comprising a first light source and first detector, providing for a second optical unit comprising a second light source and a second detector, providing for a control unit, wherein the first and the second optical units are spatially separated from each other and wherein the first and second optical units are physically linked parts of an optical detection system. Furthermore, the steps inserting the first chamber into the system and thereby aligning the first chamber with the first optical unit, inserting the second chamber into the system and thereby aligning the second chamber with the second optical unit are comprised. Additionally performing a first optical measurement of the first chamber with the first optical unit, performing a second optical measurement of the second chamber with the second optical unit, causing a movement of the first and second optical unit relative to the two chambers by the control unit are comprised wherein the relative movement is performed in such a way that the relative movement causes an aligning of the first chamber with the second optical unit and then aligning of the second chamber with the first optical unit.

The method may combine a color multiplexing using different fluorescent colors to label different PCR reactions for different pathogens or for different DNA sequences (DNA regions) of the same pathogen in a single PCR chamber with spatial multiplexing using multiple PCR chambers for different PCR reactions. The color multiplexing is achieved by having different optical units that are able to excite and detect different fluorescent spectra. Spatial multiplexing may be achieved by moving the optical units from one reaction chamber to the next one. In this way an efficient multiplexing is achieved allowing an increased number of pathogens to be screened for per time unit.

As the first and the second optical units are spatially separated they have complete different and separated optical paths from their light source to the sample and from the sample to the detector.

Furthermore the inserting and aligning of each chamber into the system is performed in such a way that an optical access between each sample chamber and the respective corresponding optical unit is established. In this way all optical units may respectively but simultaneously monitor different PCR reactions in different sample chambers. After having caused a relative movement between the optical units and the sample chambers each sample chamber can be scanned by a different optical unit which enables a user to analyze a sample and detect quantitatively and qualitatively different components of the sample like different pathogens.

After the first optical measurement at the first chamber with the first optical unit and the second optical measurement of the second chamber with the second optical unit a relative movement like for example a rotation of the optical units is caused in order to get to a second stationary position in which the first optical unit is aligned with the second sample chamber and the second optical unit is aligned with the first sample chamber.

According to another exemplary embodiment of the disclosure the method comprises the steps performing a third optical measurement of the first chamber with the second optical unit and performing a fourth optical measurement of the second chamber with the first optical unit.

After the first and second measurement a third optical measurement with the second optical unit at the first chamber may be done and a fourth optical measurement with the first optical unit at the second sample chamber may be done. In this exemplary embodiment it is possible to use different primers in the first and second sample chambers which primers have for example other fluorochrome substances. Nevertheless in this and in any other embodiment of the disclosure the fluorophore or fluorochrome can also be attached to the sample or probe and not to the primer.

In case of for example a first optical unit emitting red light and being sensitive due to a special sensor for red light and a second optical unit emitting blue light and being specifically sensitive due to a sensor for blue light one, two or more different sample chambers with different samples inside may be optically scanned so that different components of the samples may be identified. Quantification of the amount of the components may also be done on basis of the detection results.

According to another exemplary embodiment of the disclosure the method further comprises the steps providing for at least one heater and causing thermal cycling in a sample chamber with the heater.

In other words this exemplary embodiment describes a complete PCR protocol including a real-time optical readout of the amplified and targeted DNA molecule wherein a quantification of the DNA molecule can be done on the basis of the detection results of the detectors.

According to another exemplary embodiment of the disclosure the method comprises the steps providing for a PCR protocol to the control unit, controlling the heater with the control unit on the basis of the PCR protocol to cause PCR reactions in a sample chamber.

According to another exemplary embodiment of the disclosure the first and the second measurements are performed simultaneously.

Therefore the speed of a rtPCR measurement per sample can be increased, as the sample can be divided into different parts being filled into the different sample chambers. Thus duration of a pathogen detection in the sample may be reduced by the disclosure.

According to another exemplary embodiment of the disclosure a computer program element is presented which is characterized by being adapted when in use on a general purposed computer to cause the computer to perform the steps of the method according to one of the preceding embodiments.

According to another exemplary embodiment of the disclosure a computer readable medium on which a computer program element is stored is presented.

According to a further embodiment of the present disclosure a medium for making a computer program element available for downloading, which computer program element is arranged to perform the method according to one previously described embodiment of the disclosure.

The described embodiments similarly pertain to the optical multiplexing system, the method for detecting sample components, the computer program element and the computer-readable medium. Synergetic effects may arise from different combinations of the embodiment although they might not be described in detail.

Further on, it shall be noted that all embodiments of the present disclosure concerning a method, might be carried out with the order of the steps as described, nevertheless this has not to be the only and essential order of the steps of the method. All different orders and combinations of the method steps are herewith described.

The aspects defined above and further aspects, features and advantages of the present disclosure can also be derived from the examples of embodiments to be described hereinafter and are explained with reference to examples of embodiments. The disclosure will be described in more detail hereinafter with reference to examples of embodiments but to which the disclosure is not limited.

DETAILED DESCRIPTION OF THE EMBODIMENT

Figure 1:
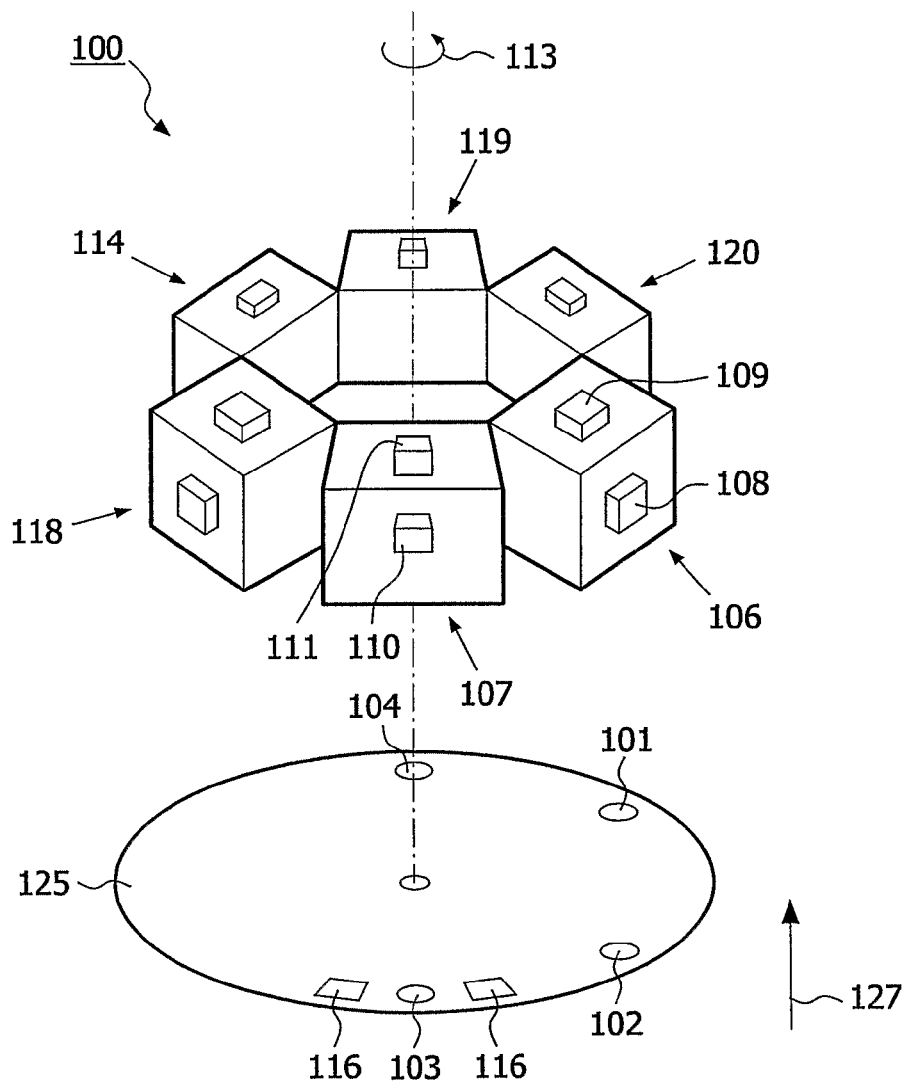
FIG. 1 schematically shows an optical multiplexing system according to an exemplary embodiment of the present disclosure.

Similar or relating components in the several figures are provided with the same reference numerals. The view in the figures is schematic and not fully scaled.

FIG. 1 shows an optical multiplexing system 100 for detecting sample components like pathogens in four different sample chambers 101, 102, 103 and 104. The system comprises a first optical unit 106 and a second optical unit 107. Thereby the first optical unit and the second optical unit are spatially separated from each other. The first optical unit comprises a first light source 108 and a first detector 109 wherein the second optical unit comprises a second light source 110 and a second detector 111. Furthermore, the system 100 is adapted for receiving the four chambers at positions that respectively correspond to one optical unit. This reception is symbolically shown by the arrow 127. For instance a motor (not shown) may be coupled to the system 100 to cause a relative movement indicated by 113. In this exemplary embodiment the relative movement is a rotation of the shown optical units 106, 107, 114, 118, 119, and 120. Thus the optical units are rotated around the stationary sample holder 125.

Each sample in one sample chamber may emit e.g. four or six different colors i.e. wavelengths. But also another quantity of colors is possible. Only one single color per chamber may be possible if desired.

Two heaters 116 are schematically shown in FIG. 1 wherein the heaters are adapted to cause a thermal cycling in at least one sample for example in the sample contained in a sample chamber 103. This schematic drawing of the heater indicates that the optical multiplexing system can be seen as a complete thermocycler performing rtPCR reactions in the four sample chambers. Therefore a PCR protocol might be provided to a control unit (not shown).

With the shown optical multiplexing system a molecular diagnostic system for automatic detection of infectious disease is provided. Thereby, the DNA detection technique of rtPCR can be implemented in the shown apparatus. Thereby a user is enabled to detect several pathogens present in one single patient sample as color multiplexing and space multiplexing are integrated inherently in the shown system.

During the processing of the PCR or any protocol the sample material can be filed into the sample chamber. Emptying the sample chambers may also be possible. To these ends leads to the sample chambers can be used.

Figure 2:
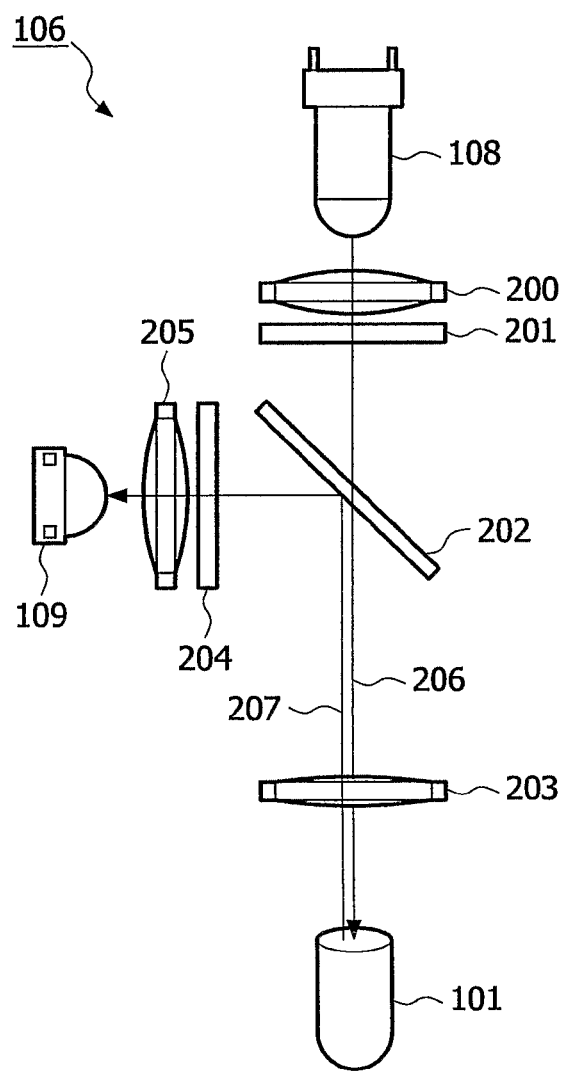
FIG. 2 shows an optical unit used in an optical multiplexing system according to another exemplary embodiment of the present disclosure.

FIG. 2 schematically shows an optical unit 106 that might be used in an optical multiplexing system 100 (not shown here) according to another exemplary embodiment of the present disclosure. Thereby the first optical unit 106 comprises a first source 108 that might be a light emitting diode. Light from the light emitting diode 108 may be collimated into a semi-parallel beam by a lens 200 and after passing an excitation filter 201 the light passes the dichroic mirror 202 to further propagate through the lens 203 focusing the photons from the LED onto the sample chamber 101. This light path is described by 206 wherein a second light path 207 is shown. 207 describes the way of the photons that are remitted by the sample in the sample chamber 101 resulting from PCR fluorescence light that is collected by the lens 203. After being reflected on the dichroic mirror 202 the fluorescence light from the sample passes the detection filter 204 and is focused with the lens 205 onto the detector 109.

Figure 3:
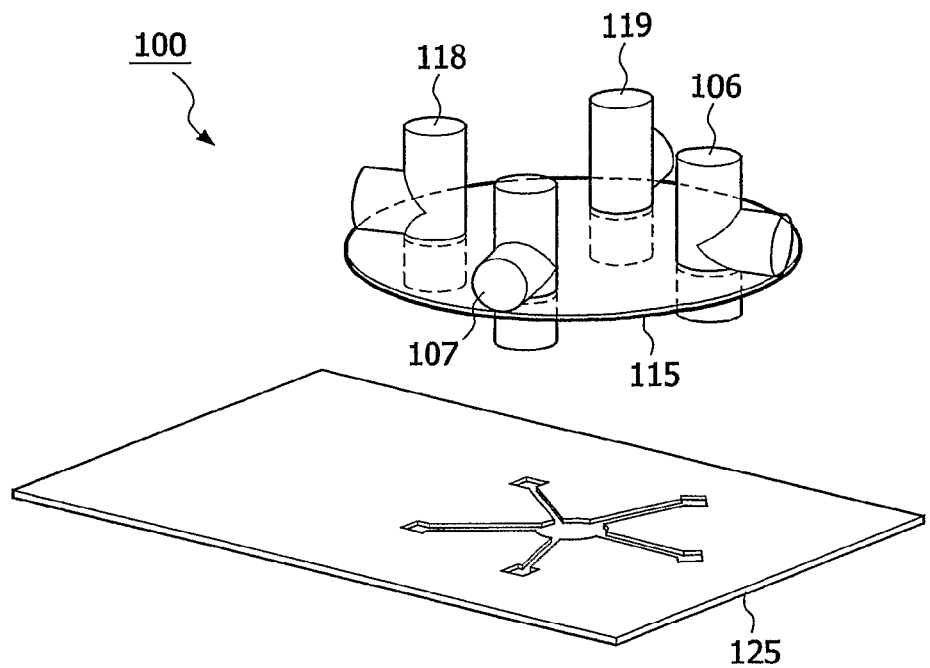
FIG. 3 schematically shows an optical multiplexing system according to another exemplary embodiment of the present disclosure.

FIG. 3 shows another exemplary embodiment of an optical multiplexing system 100 with four optical units 106, 107, 118 and 120. Furthermore a holder 125 for four different sample chambers is shown. In addition to that a rotation frame 115 can be seen with which a rotation of the optical units around the sample chambers can be caused.

Figure 4:
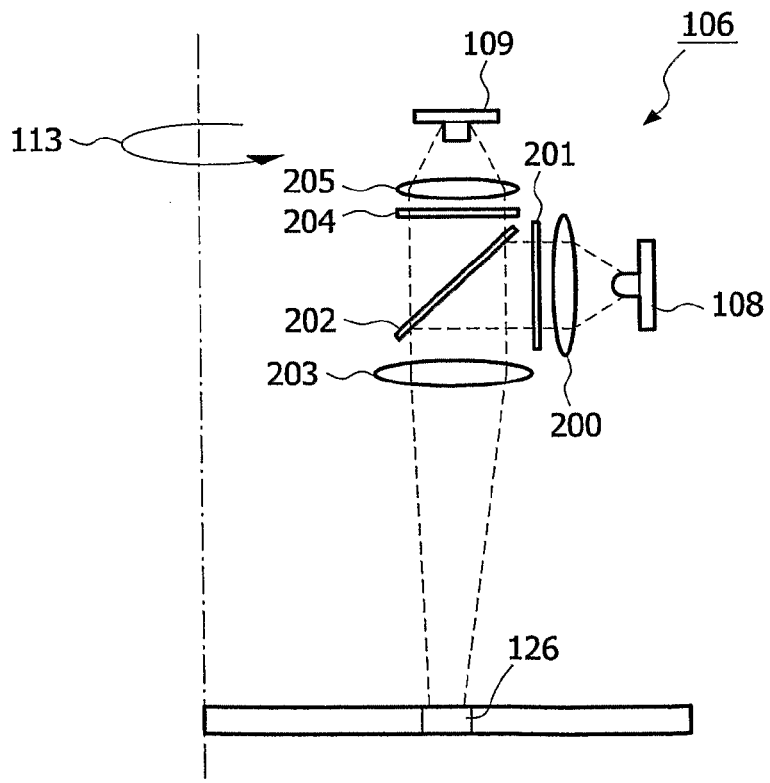
FIG. 4 schematically shows an optical unit used in an optical multiplexing system according to another exemplary embodiment of the disclosure.

FIG. 4 shows another exemplary embodiment of an optical unit 106 which unit is rotated. This may achieve space multiplexing and color multiplexing as described above. The sample 126 is illuminated with light from the first light source 108 which light is focused with the lens 200 and filtered by filter 201 wherein the dichroic mirror 202 reflects the light down to the sample 126. Reemitted light from the sample propagates from the sample through the dichroic mirror 202 and passes through the detection filter 204 and is afterwards focused by the lens 205 onto the detector 109 which is specifically designed sensitive for a specific wavelength that is emitted by a sample when illuminated with the specific wavelength emitted by the source 108.

Figure 5:
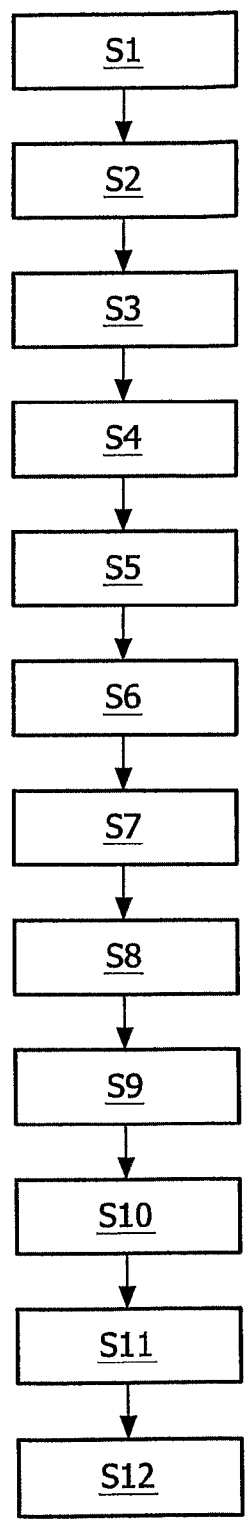
FIG. 5 schematically shows a flow diagram representing a method according to another exemplary embodiment of the present disclosure.

FIG. 5 shows a flow diagram representing a method according to another exemplary embodiment of the present disclosure. The method comprises the following steps S1 providing for a first optical unit comprising a first light source and a first detector, S2 providing for a second optical unit comprising a second light source and a second detector, S3 providing for a control unit, wherein the first and the second optical unit are spatially separated from each other and wherein the first and second optical unit are physically linked parts of an optical detection system. Furthermore S4 describes the step of inserting the first chamber into the system and thereby causing step S5 aligning the first chamber with the first optical unit. Subsequently, or also simultaneously the step inserting the second chamber into the system S6 and thereby causing the step aligning the second chamber with the second optical unit S7 is realized. Finally, the step S8 performing a first optical measurement of the first chamber with the first optical unit is done in order to detect pathogens in the sample that has been processed with PCR which pathogens are detected optically. The step S9 performing a second optical measurement of the second chamber with the second optical unit can be performed simultaneously, subsequently or partially simultaneously to the step S8. After the first and the second optical measurements the step S10 causing a movement of the first and second optical unit relative to the two chambers with the control unit is performed. Due to that relative movement the positions of the sample chambers have been changed in such a way that new pairs of samples and optical units are arranged. In other words the relative movement is performed in such a way, that the relative movement causes an aligning of the first chamber with the second optical unit which corresponds to step S11 and step S12 aligning of the second chamber with the first optical unit.

Other variations to the disclosed embodiments can be understood and effected by those skilled in the art and practicing the claimed disclosure, from the study of the drawings, the disclosure, and the appended claims. In the claims the word "comprising" does not exclude other elements or steps and the indefinite article "a" or "an" does not exclude a plurality.

A single processor or other units may fulfill the function of several items or steps recited in the claims. The mere effect that certain measures are recited in mutually different dependent claims does not indicated that a combination of these measures cannot be used to advantage. A computer program may be stored/distributed on a suitable medium such as an optical storage medium or a solid state medium supplied together with or as a part of other hardware, but may also be distributed in other forms such as via the internet or other wire or wireless telecommunication systems.

Any reference signs in the claims should not be construed as limiting the scope of the claims.

What is claimed is:

1. An optical multiplexing system for detecting sample components in at least two different sample chambers, the system comprising:
    a first optical unit for detecting a product of a first polymerase chain reaction (PCR), wherein the first optical unit comprises a first light source and a first detector;
    a second optical unit for detecting a product of a second polymerase chain reaction (PCR), wherein the second optical unit comprises a second light source and a second detector, wherein the first optical unit and the second optical unit are spatially separated from each other,
        wherein the system receives at least two sample chambers to be received at positions corresponding to the first and second optical units so that (a) the first and second light sources, respectively, simultaneously illuminate the at least two sample chambers and (b) the first and second detectors, respectively, simultaneously receive light from the at least two sample chambers, said first and second optical units simultaneously performing first and second optical measurement using two different optical wavelengths at said two spatially separated sample chambers, and wherein the system is adapted for a relative movement of the first optical unit and the second optical unit relative to the at least two sample chambers;

a first heater associated with a first sample chamber of the at least two sample chambers, said first heater creating a first temperature progression at the first sample chamber;

a second heater associated with a second sample chamber of the at least two sample chambers, said second heater creating a second temperature progression at the second sample chamber; and a control unit for receiving a PCR protocol, wherein said control unit controls the first and second heaters according to the PCR protocol to cause real time PCR reactions in the first and second sample chambers, said control unit simultaneously quantifying a targeted and amplified DNA molecule by relative movement of the first optical unit and second optical unit relative to the at least two sample chambers.

2. The optical multiplexing system according to claim 1, further comprising a motor, wherein the motor is adapted to cause the relative movement.

3. The optical multiplexing system according to claim 2, further comprising a rotation frame, wherein the first and second optical units are fixed at the rotation frame and wherein the motor causes the relative movement by rotating the rotation frame.

4. The optical multiplexing system according to claim 1, wherein the relative movement is a rotating movement.

5. The optical multiplexing system according to claim 1, wherein the relative movement is a linear movement.

6. The optical multiplexing system according to claim 1, wherein said first and second heaters cause a thermal cycling in the first and second sample chambers.

7. A molecular diagnostic device for analyzing a sample, the device comprising an optical multiplexing system according to claim 1.

8. The optical multiplexing system according to claim 1, wherein the first and second heaters have an optical transparency greater than 80% in a spectral range between 300 nm and 800 nm wavelength.

9. The optical multiplexing system according to claim 1, wherein the first and second heaters have a negligible autofluoresence at excitation wavelengths between 300 nm and 800 nm.

10. A method for detecting sample components in at least two different sample chambers, the method comprising the steps of:

receiving at least two sample chambers, each sample chamber having a sample;

aligning a first sample chamber of the at least two sample chambers with a first optical unit comprised of a first light source and a first detector;

aligning a second sample chamber of the at least two sample chambers with a second optical unit comprised of a second light source and a second detector, wherein the first optical unit and the second optical unit are spatially separated from each other;

simultaneously performing (i) a first optical measurement of a first sample chamber of the at least two sample chambers using a first optical wavelength and (ii) a second optical measurement of a second sample chamber of the at least two sample chambers using a second optical wavelength, wherein simultaneously performing the first and second optical measurements includes:

(a) simultaneously illuminating the at least two sample chambers using the first and second light sources, respectively, and (b) simultaneously receiving light from the at least two sample chambers using the first and second detectors, respectively;

moving the first optical unit and the second optical unit relative to the at least two sample chambers so as to cause an alignment of the first sample chamber with the second optical unit and an alignment of the second sample chamber with the first optical unit;

heating the first sample chamber of the at least two sample chambers with a first heater to create a first temperature progression at the first sample chamber;

heating the second sample chamber of the at least two sample chambers with a second heater to create a second temperature progression at the second sample chamber; and controlling the first and second heaters according to a PCR protocol to cause real time PCR reactions in the first and second sample chambers, and simultaneously quantifying a targeted and amplified DNA molecule by relative movement of the first optical unit and the second optical unit relative to the at least two sample chambers.

11. The method according to claim 10, further comprising the steps of:

performing a third optical measurement of the first sample chamber with the second optical unit; and performing a fourth optical measurement of the second sample chamber with the first optical unit.

12. The method according to claim 10, further comprising:

causing thermal cycling in the first and second sample chambers with the first and second heaters.

13. A computer program element characterized by being adapted, when in use on a general purpose computer, to cause the computer to perform the steps of:

aligning a first sample chamber with a first optical unit comprising a first light source and a first detector;

aligning a second sample chamber with a second optical unit comprising a second light source and a second detector, wherein the first optical unit and the second optical unit are spatially separated from each other and the first optical unit and second optical unit are physically linked parts of an optical detection system;

simultaneously performing (i) a first optical measurement of the first sample chamber using a first optical wavelength and (ii) a second optical measurement of a second sample chamber using a second optical wavelength, wherein simultaneously performing the first and second optical measurements includes:

(a) simultaneously illuminating the first and second sample chambers using the first and second light sources, respectively, and (b) simultaneously receiving light from the first and second sample chambers using the first and second detectors, respectively;

heating the first sample chamber with a first heater to create a first temperature progression at the first sample chamber;

heating the second sample chamber with a second heater to create a second temperature progression at the second sample chamber;

controlling the first and second heaters according to a PCR protocol to cause real time PCR reactions in the first and second sample chambers, and simultaneously quantifying a targeted and amplified DNA molecule by relative movement of the first optical unit and the second optical unit relative to the first and second sample chambers; and moving the first optical unit and the second optical unit relative to the first and second sample chambers so as to cause an alignment of the first sample chamber with the second optical unit and an alignment of the second sample chamber with the first optical unit.

14. A non-transitory computer readable medium storing instructions of a computer program which, when executed by a computer, result in the performance of the steps according to claim 13.

15. An optical multiplexing system for detecting sample components in at least two sample chambers, the system comprising:
 a first optical unit having a first light source and a first detector, said first optical unit detecting a product of a first polymerase chain reaction (PCR);
 a second optical unit having a second light source and a second detector, said second optical unit detecting a product of a second polymerase chain reaction (PCR), wherein the second optical unit is spatially separated from the first optical unit;
 a first heater associated with a first sample chamber of the at least two sample chambers, said first heater creating a first temperature progression at the first sample chamber;
 a second heater associated with a second sample chamber of the at least two sample chambers, said second heater creating a second temperature progression at the second sample chamber;
 a rotation frame having the first and second optical units fixed thereto;
 a motor adapted to rotate the rotation frame so as to cause the first and second optical units to move between a first position and a second position,
 wherein, when in the first position, the first optical unit is positioned with respect to a first sample chamber and the first heater so that the first light source illuminates and the first detector receives light from the first sample chamber, while the second optical unit is positioned with respect to a second sample chamber and the second heater so that the second light source illuminates and the second detector receives light from the second sample chamber, and
 said first and second optical units simultaneously illuminate the at least two sample chambers, and the first and second detectors simultaneously receive light from the at least two sample chambers, wherein said first and second optical units simultaneously perform first and second optical measurement using two different optical wavelengths at said at least two sample chambers; and
 a control unit for receiving a PCR protocol, wherein said control unit controls the first and second heaters according to the PCR protocol to cause real time PCR reactions in the first and second sample chambers, said control unit simultaneously quantifying a targeted and amplified DNA molecule by relative movement of the first optical unit and second optical unit relative to the at least two sample chambers.

16. The optical multiplexing system according to claim 15, wherein, when in the second position, the first optical unit is positioned with respect to the second sample chamber and the second heater so that the first light source illuminates and the first detector receives light from the second sample chamber, while the second optical unit is positioned with respect to the first sample chamber and the first heater so that the second light source illuminates and the second detector receives light from the first sample chamber.

17. The optical multiplexing system according to claim 15, wherein the first and second heaters are optically transparent to said first and second light sources, said first and second heaters have an optical transparency greater than 80% in a spectral range between 300 nm and 800 nm wavelength.

18. The optical multiplexing system according to claim 15, wherein the first and second heaters have a negligible autofluoresence at excitation wavelengths between 300 nm and 800 nm.

19. An optical multiplexing system for detecting sample components in at least two sample chambers, the system comprising:
 a first optical unit comprising a first light source and a first detector, said first optical unit detecting a product of a first polymerase chain reaction (PCR);
 a second optical unit comprising a second light source and a second detector, said second optical unit detecting a product of a second polymerase chain reaction (PCR), wherein the first and second optical units are spatially separated from each other,
  wherein the system receives at least two sample chambers to be received at positions corresponding to the first and second optical units so that the first and second light sources, respectively, simultaneously illuminate the at least two sample chambers, and the first and second detectors, respectively, simultaneously receive light from the at least two sample chambers, said first and second optical units simultaneously performing first and second optical measurements using two different optical wavelengths at said two spatially separated sample chambers;
 a first heater associated with a first sample chamber of the at least two sample chambers, said first heater creating a first temperature progression at the first sample chamber;
 a second heater associated with a second sample chamber of the at least two sample chambers, said second heater creating a second temperature progression at the second sample chamber; and
 a control unit for receiving a PCR protocol, wherein said control unit controls the first and second heaters according to the PCR protocol to cause real time PCR reactions in the first and second sample chambers, said control unit simultaneously quantifying a targeted and amplified DNA molecule by relative movement of the first optical unit and second optical unit relative to the at least two sample chambers,
 wherein the system is adapted for:
  performing a first optical measurement of the first sample chamber with the first optical unit,
  performing a second optical measurement of the second sample chamber with the second optical unit, and
  a relative movement of the first and second optical units relative to the at least two sample chambers in order to get to a second stationary position in which the first optical unit is aligned with the second sample chamber and the second optical unit is aligned with the first sample chamber.

* * * * *

UNITED STATES PATENT AND TRADEMARK OFFICE
CERTIFICATE OF CORRECTION

PATENT NO. : 8,441,629 B2 Page 1 of 1
APPLICATION NO. : 13/273801
DATED : May 14, 2013
INVENTOR(S) : Kolesnychenko et al.

It is certified that error appears in the above-identified patent and that said Letters Patent is hereby corrected as shown below:

On title page, item (30) Foreign Application Priority Data, line 1, replace
"Apr. 15, 2009  (EP) ......09157910" with "Apr. 15, 2009  (EP) ......09157910.2"

Signed and Sealed this
Eleventh Day of June, 2013

Teresa Stanek Rea
*Acting Director of the United States Patent and Trademark Office*